United States Patent [19]

Schlueter et al.

[11] 4,151,274

[45] Apr. 24, 1979

[54] PROCESS AND COMPOSITION FOR THE PRODUCTION OF SUPPOSITORIES

[75] Inventors: Karl W. Schlueter, Hamburg; Eckhard Schulz-Kaiser, Halstenbek, both of Fed. Rep. of Germany

[73] Assignee: Karl-Werner Schlueter G.m.b.H., Hamburg, Fed. Rep. of Germany

[21] Appl. No.: 741,986

[22] Filed: Nov. 15, 1976

[30] Foreign Application Priority Data

Nov. 15, 1975 [DE] Fed. Rep. of Germany ....... 2551446

[51] Int. Cl.$^2$ ................................................ A61K 9/02
[52] U.S. Cl. ..................................... 424/80; 128/271; 264/5; 264/126; 424/14; 424/78; 424/358; 424/362; 424/365
[58] Field of Search ..................... 128/271; 424/14, 19, 424/22, 78, 80, 362, 365; 264/5, 126

[56] References Cited

U.S. PATENT DOCUMENTS

| | | | |
|---|---|---|---|
| 2,820,741 | 1/1958 | Endicott et al. | 424/80 |
| 2,975,099 | 3/1961 | Goyan et al. | 424/181 |
| 3,102,845 | 9/1963 | Fennell | 424/80 |
| 3,121,663 | 2/1964 | Parker | 424/78 |
| 3,133,863 | 5/1964 | Tansey | 424/22 |
| 3,136,692 | 6/1964 | Bandelin | 424/80 |
| 3,234,091 | 2/1966 | Lang et al. | 424/14 |
| 3,266,992 | 8/1966 | de Jong | 424/131 |
| 3,632,778 | 1/1972 | Sheth et al. | 424/80 |
| 3,679,794 | 7/1972 | Bentholm et al. | 424/362 X |
| 3,826,823 | 7/1974 | O'Rourke et al. | 424/80 |

FOREIGN PATENT DOCUMENTS 1128600  4/1962  Fed. Rep. of Germany.

*Primary Examiner*—Shep K. Rose
*Attorney, Agent, or Firm*—Schwartz, Jeffery, Schwaab, Mack, Blumenthal & Koch

[57] ABSTRACT

Disclosed are a composition and process for the production of suppositories wherein a mixture comprising at least one ester out of the group of glycols preferably 1,2-propyleneglycol esterified with one saturated higher fatty acid such as myristic, palmitic and stearic acid and at least one pharmacologically active ingredient is formed, this mixture then is granulated with a solution of at least one film-forming polymer and the resulting granulate is pressed into suppositories on a tableting machine.

17 Claims, No Drawings

PROCESS AND COMPOSITION FOR THE PRODUCTION OF SUPPOSITORIES

BACKGROUND OF THE INVENTION

The present invention pertains to the manufacture of suppositories and more especially to the manufacture of suppositories from one or more glycol esters of higher saturated fatty acids and at least on pharmacologically effective agent.

The production of suppositories containing the above mentioned components is already known from German Patent No. 1,128,600. Yet up to now these suppositories of such composition are produced by melting processes. According to such processes the ingredients are first melted by heating and the molten composition is then filled into appropriate molds. After cooling the molds are opened and the suppositories removed. Because of the necessary heating and cooling operations such a process is extremely expensive and time consuming.

Suppositories have previously been produced by pressing methods. According to known pressing methods, a mixture of the ingredients is compressed by means of a plunger or a screw and then is injected into appropriate molds by extrusion through a nozzle. This causes a plastic deformation of the suppository material. Only a very low speed of production can be achieved by such a method because of the complicated procedure.

SUMMARY OF THE INVENTION

It is therefore an object of the present invention to provide a process for producing suppositories with high speed and without applying extensive heating and cooling operations and to provide a tabletable composition which can be used for producing suppositories.

Another object of this invention is to provide a process for the production of suppositories which exhibit a preferably sharp melting point at a temperature of several degrss below human body temperature, preferably a temperature between 34° and 37° C.

It is a further object of this invention to provide a process for producing suppositories, which exhibit a melting point of several degrees below human body temperature, using starting materials which melt at temperatures above human body temperature without effecting any melting operation.

It is still further an object of this invention to provide a process for producing suppositories which allows the use of starting materials, which do not react in any way with the incorporated pharmacologically effective agents, and specifically a process which allows the use as starting materials of esters of any appropriate hydroxyl value, specially a hydroxyl value below 1. It is a further object of this invention to provide a process for the production of suppositories by which heating of the incorporated pharmacologically active ingredients can be avoided.

A further object of this invention is to provide a process for the production of suppositories, by which an exact dosage and a uniform distribution of the pharmacologically active ingredients within the suppositories can be accomplished and any sedimentation of said active ingredients can be avoided.

It is yet another object of this invention to provide a process for the production of suppositories which can be effected by means of an apparatus which is significantly simpler than the complicated equipment presently necessary for melting and solidification and which enables the production of suppositories to be carried out economically.

In accomplishing the foregoing objects there has been provided in accordance with the present invention a process for the production of suppositories and tablets comprising the steps of (a) forming a mixture of at least one ester selected from the group of glycols esterified with one higher saturated fatty acid and at least one pharmacologically active ingredient; (b) granulating this mixture with a solution of at least one film-forming physiologically acceptable polymer; and (c) pressing the granulate into shaped pieces.

According to the invention the pressing of the granulate may be effected on a tableting machine. It is advisable to effect the pressing at a temperature somewhat below normal room temperature, e.g, between room temperature and $-10°$ more especially between 0° and $+10°$ C.

Among the higher saturated fatty acids, the following ones are preferably used as a component of the glycol esters: myristic acid, palmitic acid, and/or stearic acid. As glycols the following are preferably used: ethylene glycol triethylene glycol, propylene glycol and/or butylene glycols. According to a preferred embodiment of the invention 1,2-propylene glycol is used as a component of the esters for the production of suppositories or tablets. More specifically 1,2 propylene glycol myristate, palmitate and/or stearate may be used in forming said mixture. The use of 1,2-propylene glycol is especially preferred because it is completely non-toxic.

Surprisingly, it was found that the pressed articles exhibit a melting point below human body temperature, in spite of the facts that no melting took place and that all esters of propylene glycol and myristic palmitic or stearic acid exhibit a melting point above human body temperature.

According to a preferred embodiment of the invention, in forming said mixture there is used an excess of glycol myristate preferably 1,2-propylene glycol myristate in order to adjust the suppositories to exhibit a sharp melting point, preferably a melting point between about 34°-37° C. The amount of added myristate may be, for example, as much as about 80% of the ester composition in said mixture, whereas the remaining part of this ester composition may comprise at least one ester selected from the group of glycol palmitates and stearates preferably 1,2-propylene glycol palmitate and 1,2-propylene glycol stearate.

Other objects, features and advantages of the invention will become apparent from the detailed description of some preferred embodiments which follows.

DETAILED DESCRIPTION OF PREFERRED EMBODIMENTS

The invention provides a process for the production of suppositories and tablets which comprises as a first step forming a mixture of at least one ester selected from the group of glycols esterified with one higher saturated fatty acid and at least one pharmacologically active ingredient. As a glycol component of said esters there may be used ethylene glycol, methylene glycols, propylenglycols and/or butylene glycols, preferably 1,2-propyleneglycol. As an acid component may be used saturated fatty acids, which contain between 12 and 20 carbon atoms, especially myristic acid, preferrably in excessive amounts, e.g. amounts of about 80% of the mixture, palmitic acid or stearic acid.

Due to the fact that such glycol esters can be produced which exhibit a maximum hydroxyl value of 1, no reaction between these esters and the pharmacologically active ingredients is to be expected.

Optionally at least one ester selected from the group of glycerine being completely esterified with one fatty acid can be used as an additional part of the above mixture of esters. Glycerine trilaurate has proved specially useful for this purpose.

The resulting mixture is then granulated preferably in a wet granulating process using a solution of at least one film-forming physiologically acceptable polymer and the resulting granulate is dried and the dried granulate is then pressed into shaped bodies. In effecting this granulation, at least one binding agent is applied which may be selected from the group of hydrophilic physiologically acceptable polymers with film-forming properties, such as a cellulose derivative, e.g., carboxy-methylcellulose, carboxy-hydroxy-methylcellulose, carboxethylcellulose and so on, or a polyvinylic compound, e.g., polymers of N-vinyllactames as polyvinylpyrrolidone or copolymers of vinylpyrrolidone, e.g., with acrylic acid. These binding agents may be used in amounts of 1-6% preferably 1-3% of the entire mixture.

As is common in the production of tablets, at least one binding agent is added to the mixture which is to be pressed, then the mixture is moistened with an aqueous or organic solvent for said binding agent. The binding agents can also be added in the form of an aqueous or organic solution.

In order to keep the adhesion of the pressed bodies to the pressing molds as low as possible, it is advantageous to add appropriate lubricants to the material or to cover it with such lubricants. Substances like the following may be used as lubricants: Magnesium stearate, silicic acid, talcum or silicone oils. These lubricants may be used in amounts of about 2-5% of the entire mixture.

The mixture which is composed according to the invention is now granulated according to known methods. Surprisingly, these esters of glycols and fatty acids are found to be especially suited for being granulated, due to their physical structure. If desired, further additives like preserving agents and the like may be incorporated into the mixture during the granulation process.

The granulation can be effected, e.g., by spray drying with the addition of organic or inorganic solvents. The method of so-called granulation by sintering may also be used. In this method the pulverous substances are heated until soft and the mass is then kneaded, whereby melting has of course to be avoided. After cooling the mass is pressed through a sieve plate or the like, whereby the desired granulate is obtained. These methods as well as other possible methods for granulation, e.g., in rotating drums with addition of solvents, are known from the tablet production industry.

The pressing of the granulate may be effected on a tableting machine such as usual excentric or rotary tableting machines, such as are applied in tablet pressing processes, whereby appropriately formed pressing dies must be inserted for producing suppositories. It is advisable to effect the pressing at a temperature somewhat below normal room temperature e.g., around 15° C.

The invention is further explained by the following examples, which are illustrative only.

PRODUCTION OF STARTING MATERIALS 500 g of myristiric acid (percentage purity: 98% iodine number: (1) are esterified with 87 g 1,2-propylenglycol in the presence of 1 g of zinc dust in the conventional manner. After refining, washing and drying the resulting ester exhibits an iodine number below 1, a hydroxyl number of 0.85 and a melting point of 38° C.

In a separate reaction 500 g of palmitic acid (percentage purity: 96%, iodine number: (1) are esterified with 1,2-propylene glycol in the presence of 1 g of zinc dust in the usual way. After refining washing and drying the resulting product exhibits an iodine number below 1, and a hydroxyl number of 0.9.

In a third preparation 500 g of stearic acid are esterified with 67 g. of propylene glycol in the presence of 1 g of zinc dust. After refining, washing and drying the resulting ester exhibits a hydroxyl number of 0.8.

EXAMPLE 1

80 parts by weight (g.) of the above described propylene glycol myristate and 20 parts by weight of the above described propylene glycol palmitate in powdery form are mixed together. 40 g of acetylsalicylic acid are added. In a stirring apparatus the dry mixture is moistened by a solution of 15 g of polyvinyl pyrrolidone in 25 ml of isopropanol, and stirring is continued until a uniform intermixture is achieved. This material is pressed through a sieve plate of 1 mm mesh size and subsequently dried on a hurdle tray at a temperature not exceeding 25° C. In order to obtain completely uniform granulates it is recommendable to pass the material once more through a sieve. This finished granulate can then be pressed on a rotary tableting machine without difficulty at a temperature of about 15° C.

EXAMPLE 2

80 parts by weight (g.) of the above-described propylene glycol myristate 15 parts by weight of the above-described propyleneglycol palmitate and 5 parts by weight of propylene glycol stearate in dry form are mixed together. 0.1 g of ergotamine tartrate are added and thorough mixing of the entire material is continued. The material is moistened with an aqueous solution containing 2,5% of carboxymethyl cellulose and granulated as described above. These granulates also have outstanding pressing properties and yield molded pieces which exhibit a sharp melting point which is located within the range suited for suppositories.

Into the above-mentioned suppository materials other usual pharmacologically active agents can be incorporated in the same manner, e.g., amidopyrine methane sulfonate (Novalgin) barbiturates, sulfonamides, antibiotics, dimethylphenyl pyrazolone (pyramidon) and the like.

Instead of the above-mentioned binding agents there can also be used other cellulose derivatives or polyvinyl copolymers in known manner.

The process for the production of suppository material according to this invention provides the advantage that no heating of the pharmologically active agents occurs, which has been unavoidable in the heretofore usual melting method. Besides, by mixing the starting materials the amount of active ingredients can be dosed very exactly, whereas with the melting method a sedimentation of the active ingredients easily occurs within the melted suppository material, so that a uniform dosage becomes uncertain. Besides, the present process naturally requires mechanical equipment which is much simpler than the previously necessary complicated equipment for melting and solidification in suppository production. Thus, the present process becomes essentially more economical, since by a usual tableting machine at least 50 tablets per minute can be produced without difficulty. This means an acceleration of the production which could never be obtained by a melting process.

The invention provides special advantage in that any chemical reaction of the pharmacologically active ingredients with the esters has been rendered impossible, because of the complete freedom as to the hydroxyl value of the esters to be used. Thus the new suppositories show a practically unlimited storage stability.

What is claimed is:

1. A process for the production of suppositories comprising the steps of:
   (a) mixing a major portion of 1,2-propylene glycol myristate with a minor portion of at least one 1,2-propylene glycol ester selected from the group consisting of 1,2-propylene glycol palmitate and 1,2-propylene glycol stearate in dry form with at least one pharmacologically active ingredient for suppositories to form a dry mixture;
   (b) moistening the mixture with the solution of at least one film-forming physiologically acceptable hydrophilic polymer binding agent in an aqueous or organic solvent for said binding agent to form a uniformly moistened mixture at a sufficiently low temperature to avoid melting of the mixture;
   (c) pressing the moistened mixture through a sieve plate to obtain a granulate;
   (d) drying the granulate at a sufficiently low temperature to avoid melting of the granulate; and
   (e) pressing the granulate into suppositories at a temperature of between $-10°$ C. and room temperature in a high speed eccentric or rotary tableting machine capable of producing at least about 50 tablets per minute.

2. The process according to claim 1, wherein said major portion of 1,2-propylene glycol myristate and said minor portion of 1,2-propylene glycol esters are mixed in a ratio of about 80:20.

3. The process according to claim 1, wherein said forming step comprises forming a mixture wherein said esters of glycols have a hydroxyl value below about 1.

4. The process according to claim 1, wherein said moistening step comprises adding at least one of said film-forming polymers and a solvent for this polymer to said mixture.

5. The process according to claim 1, wherein said moistening step comprises moistening said moisture with a solution of at least one hydrophilic physiologically acceptable polymer with film-forming properties.

6. The process according to claim 5, wherein said moistening step comprises moistening said mixture with a solution containing at least one cellulose derivative.

7. The process according to claim 6, wherein said moistening step comprises moistening said mixture with a solution containing carboxymethyl cellulose.

8. The process according to claim 5, wherein said moistening step comprises moistening said mixture with a solution containing at least one polyvinylic compound.

9. The process according to claim 8, wherein said moistening step comprises moistening said mixture with a solution containing polyvinylpyrrolidone.

10. The process according to claim 9, wherein said moistening step comprises moistening said mixture with a solution containing polyvinylpyrrolidone of an average molecular weight between 25,000 and 40,000.

11. The process according to claim 5, wherein said moistening step comprises moistening said mixture with a solution containing said polymer in amounts of about 1 to 6% by weight of the entire mixture.

12. The process according to claim 11, wherein said moistening step comprises moistening said mixture with a solution containing said polymers in amounts of about 1 to 3%, by weight of the entire mixture.

13. The process according to claim 1, wherein said process further comprises adding a lubricant to said mixture before said pressing step.

14. The process according to claim 13, wherein said lubricant is added in an amount of 2-5% of the entire mixture.

15. A high speed eccentric or rotary machine-pressed suppository prepared according to the process of claim 1 comprising major portion of 1,2-propylene glycol myristate, a minor portion of at least one 1,2-propylene glycol ester selected from the group consisting of 1,2-propylene glycol palmitate and 1,2-propylene glycol stearate, at least one pharmacologically active ingredient, and at least one film-forming physiologically acceptable hydrophilic polymer binding agent.

16. A suppository as defined in claim 15, which comprises 1-6% of said polymer.

17. A suppository as defined in claim 15, which comprises at least about 80% of 1,2-propylene glycol myristate.

* * * * *